US007402295B2

(12) United States Patent
Geckeler et al.

(10) Patent No.: US 7,402,295 B2
(45) Date of Patent: Jul. 22, 2008

(54) OXYFULLERENE HOLLOW NANOSPHERES AND PROCESS FOR THE PREPARATION THEREOF

(75) Inventors: Kurt Ernst Geckeler, Gwangju (KR); Yulan Wang, Gwangju (KR)

(73) Assignee: Gwang Ju Institute of Science and Technology

( * ) Notice: Subject to any disclaimer, the term of this patent is extended or adjusted under 35 U.S.C. 154(b) by 423 days.

(21) Appl. No.: 10/947,596

(22) Filed: Sep. 22, 2004

(65) Prior Publication Data

US 2005/0063966 A1    Mar. 24, 2005

(30) Foreign Application Priority Data

Sep. 23, 2003    (KR) ..................... 10-2003-0065751

(51) Int. Cl.
*C01B 31/02*    (2006.01)
(52) U.S. Cl. .................... 423/445 B; 977/737; 977/847
(58) Field of Classification Search ............. 423/445 B; 977/740

See application file for complete search history.

(56) References Cited

FOREIGN PATENT DOCUMENTS

| EP | 0 625 055 B1 | 5/2000 |
|----|--------------|--------|
| EP | 1 071 149 A2 | 1/2001 |

OTHER PUBLICATIONS

Dresselhaus, et al., Science of Fullerenes and Carbon Nanotubes, 60-79 (Academic Press, Inc. 1996).*
Wang, et al., Hollow porous carbon nanospheres with large surface area and stability, assembled from oxidized fullerenes, J. Mater. Chem., 2005, 15, 1049-1054.*

* cited by examiner

*Primary Examiner*—Stuart L. Hendrickson
*Assistant Examiner*—Daniel C. McCracken
(74) *Attorney, Agent, or Firm*—Baker & Hostetler, LLP

(57) ABSTRACT

A novel oxyfullerene hollow nanosphere of $C_xO_yMn_z$ ($45 \leq x \leq 72$, $18 \leq y \leq 42$, $7 \leq z \leq 16$; x, y and z are atomic percentages) has a large surface area and high thermal stability, and can be simply prepared by reacting fullerene with alkali metal hydroxide and $KMnO_4$ or $MnO_2$, and treating the resulting mixture with an acid.

9 Claims, 15 Drawing Sheets

US 7,402,295 B2

OXYFULLERENE HOLLOW NANOSPHERES AND PROCESS FOR THE PREPARATION THEREOF

FIELD OF THE INVENTION

The present invention relates to a novel oxyfullerene-based hollow nanosphere, and a process for the preparation thereof.

DESCRIPTION OF THE PRIOR ART

Fullerene having a truncated $C_{60}$ icosahedron structure has recently been found to possess outstanding electronic, conducting and magnetic properties as well as enzyme inhibition, anticancer and DNA-cleaving activities, and accordingly, fullerene and its derivatives are used in many fields including medical science and pharmaceutical chemistry.

The present inventors have endeavored to develop a hollow nanosphere having improved physicochemical properties; and have unexpectedly found that a new kind of oxyfullerene-based nanosphere exhibits unique properties.

SUMMARY OF THE INVENTION

Accordingly, it is a primary object of the present invention to provide a novel hollow nanosphere having improved physicochemical properties.

It is another object of the present invention to provide a simple and efficient process for the preparation of an oxyfullerene-based hollow nanosphere.

In accordance with one aspect of the present invention, there is provided an oxyfullerene hollow nanosphere of formula (I):

$$C_xO_yMn_z \qquad (I)$$

wherein x, y and z are atomic percentages, and in the ranges of 45 to 72, 18 to 42 and 7 to 16, respectively.

In accordance with another aspect of the present invention, there is provided a method for preparing the oxyfullerene hollow nanosphere of formula (I) comprising (i) reacting a fullerene with an alkali metal hydroxide, and potassium permanganate or manganese dioxide; (ii) treating the solid obtained in step (i) with an acidic solution; and (iii) removing the liquid phase to collect the solid obtained in step (ii), followed by washing the solid.

BRIEF DESCRIPTION OF THE DRAWINGS

The above and other objects and features of the present invention will become apparent from the following description of the invention, when taken in conjunction with the accompanying drawings, which respectively show.

DETAILED DESCRIPTION OF THE INVENTION

Figure 1A:
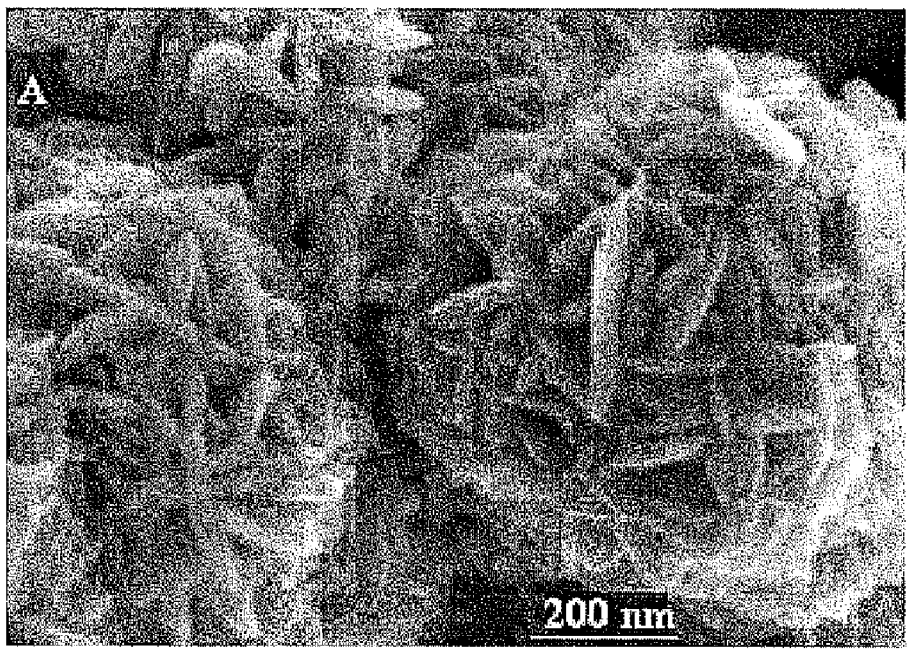
FIGS. 1A to 1D: Scanning electron microscopy (SEM) images of oxyfullerene ($oxyC_{60}$) prepared in Step 1 of Example 1.
Figure 1B:
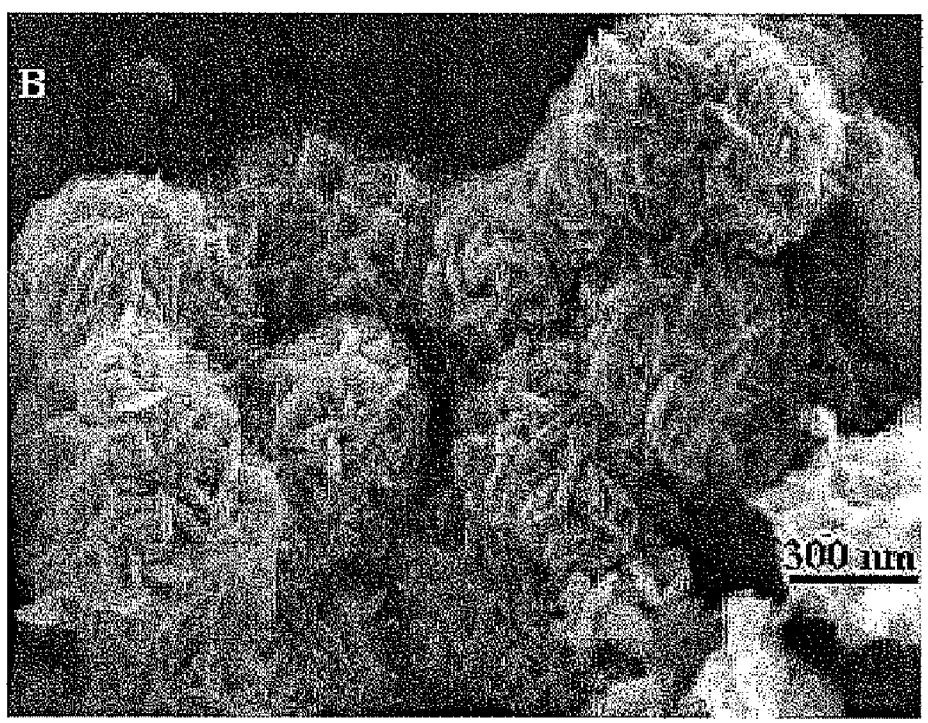
Figure 1C:
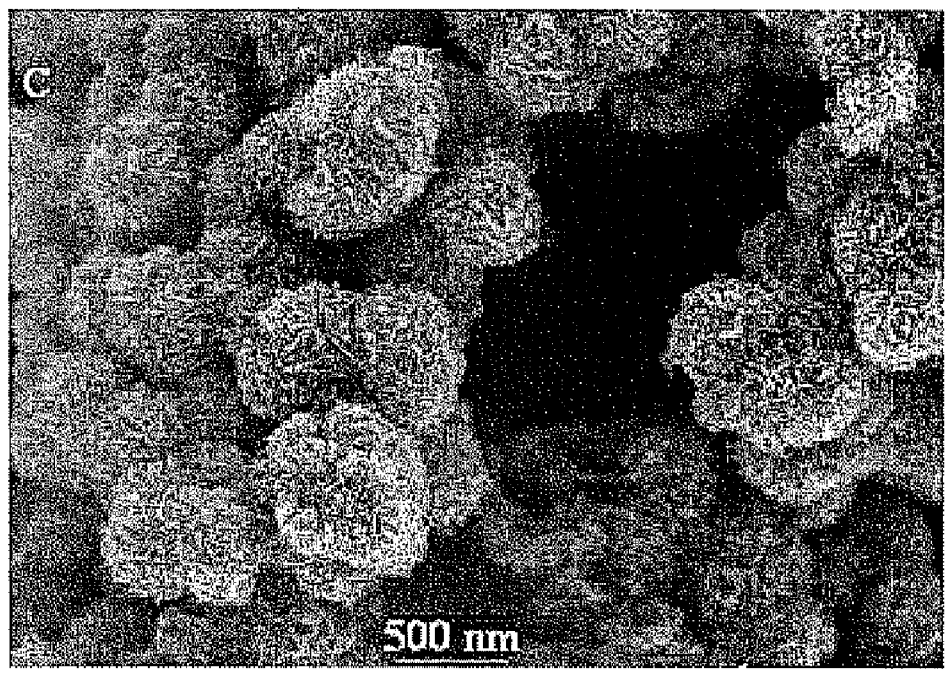
Figure 1D:
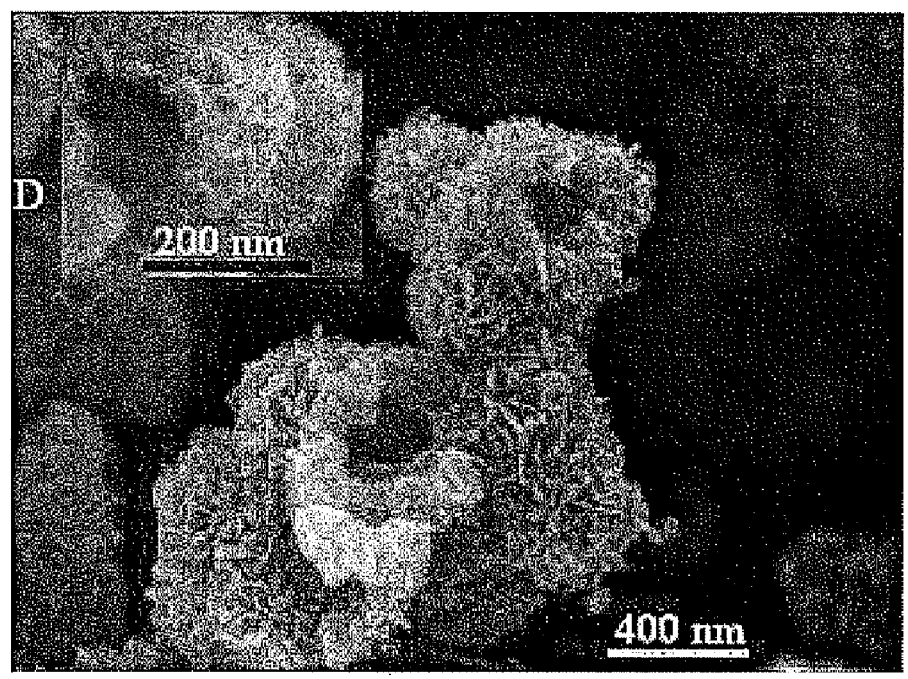

The inventive novel oxyfullerene hollow nanosphere is represented by formula (I):

$$C_xO_yMn_z \qquad (I)$$

wherein x, y and z are atomic percentages, and in the ranges of 45 to 72, 18 to 42 and 7 to 16, respectively.

The inventive compound of formula (I) may be prepared by a process comprising (i) reacting a fullerene with an alkali metal hydroxide, and potassium permanganate ($KMnO_4$) or manganese dioxide ($MnO_2$), (ii) treating the solid obtained in step (i) with an acidic solution, and (iii) removing the liquid phase to collect the solid obtained in step (ii), followed by washing the solid.

In a preferred embodiment of the present invention, the inventive process may further comprise (iv) combining the liquid filtrate and the wash solution generated during the collecting and washing processes in step (iii), (v) treating the resulting mixture with an alkaline aqueous solution, and (vi) collecting and washing the resulting solid.

In a preferred embodiment of the present invention, steps (iv) to (vi) may be repeated once or more, to raise the yield of the desired oxyfullerene nanosphere.

In the inventive process, the reaction of the fullerene with the alkali metal hydroxide and $KMnO_4$ or $MnO_2$ in step (i) may be carried out simultaneously or successively. Representative examples of the alkali metal hydroxide used in step (i) may be potassium hydroxide (KOH) and sodium hydroxide (NaOH), which may be employed in the reaction in amounts of 12 to 20 folds by weight based on the weight of the fullerene. Also, $KMnO_4$ or $MnO_2$ may be employed in the reaction in amount of 3 to 6 folds by weight based on the weight of the fullerene.

In the present invention, the acid used in step (ii) may be concentrated HCl, and the alkaline aqueous solution in step (v) may be aqueous NaOH.

The oxyfullerene hollow nanospheres obtained by the inventive process have a large surface area and good thermal stability, and thus, can be beneficially employed in various fields.

The following Examples are given for the purpose of illustration only and are not intended to limit the scope of the invention.

Preparation of the Compounds of Formula (I)

EXAMPLE 1

Step 1: Preparation of $C_{60}O_{53}Mn_{16}$ 180 mg of potassium hydroxide and 50 mg of potassium permanganate were placed in a stainless steel capsule containing stainless milling balls. The capsule was vigorously shaken in a Retsch 200 mm miller at a frequency of 30 in air at room temperature for 30 min, and 10.5 mg of fullerene ($C_{60}$) was added thereto. After 2 hours, 12 ml (2 ml×6) of water was added thereto, the resulting mixture was centrifuged, and the supernatant was removed to obtain a dark brown solid. Such washing process was repeated until the wash solution became neutral to ensure complete removal of potassium hydroxide and potassium permanganate, and the resulting wet solid was dried at 70° C. overnight to obtain 28.7 mg of a black solid.

The solid was stirred with 0.3 ml of concentrated HCl for 1 h, and 1.7 ml of water was added thereto with stirring. The resulting mixture was centrifuged and the supernatant was removed to obtain a brown solid. The solid was mixed with water, the mixture was centrifuged and the supernatant was removed. Such washing process was carried out repeatedly until the wash solution became neutral. The resulting wet solid was dried at 70° C. overnight to obtain 10.4 mg (yield 29%) of the title compound (percent composition: C/O/Mn=46.5/41.1/12.4).

Step 2: Preparation of $C_{60}O_{40}Mn_{12}$

The supernatants separated during the second washing process of Step 1 were combined, and a 10% NaOH aqueous solution was added thereto until pH of the reaction solution became 9. After centrifuging, the liquid phase was removed and the resulting crystal was mixed with water. Such washing process was carried out repeatedly until the wash solution become neutral. The resulting wet solid was dried at 70° C. overnight to obtain 9.0 mg (yield 30.9%) of the title compound as a black solid (percent composition: C/O/Mn=53.6/35.7/10.7).

Step 3: Preparation of $C_{60}O_{15}Mn_8$

The liquid phase and wash solution generated during the process of Step 2 were combined, and 10% NaOH was added thereto until pH of the reaction solution became 13. The resulting brown crystal was isolated and washed according to the procedure of Step 2 to obtain 7.5 mg (yield 37.1%) of the title compound as a black solid (percent composition: C/O/Mn=72.3/18.1/9.6).

Total yield was 29+30.9+37.1=97%.

EXAMPLE 2

Step 1: Preparation of $C_{60}O_{53}Mn_{16}$ 12 mg of fullerene and 172 mg of potassium hydroxide were placed in a stainless steel capsule containing stainless milling balls, and the capsule was vigorously shaken (frequency 30) in air at room temperature for 2 hours. After adding 16 ml of water (4 ml×4) thereto, the mixture was carefully transferred to a reactor, and stirred with 54.1 mg of solid potassium permanganate at room temperature for 2.5 hours. The reaction mixture was centrifuged, and the supernatant was removed. The residue was mixed with 12 ml of water, centrifuged, and the supernatant was removed. Such washing process was repeated until the wash solution become neutral to ensure complete removal of potassium hydroxide and potassium permanganate. The resulting wet solid was dried at 70° C. overnight to obtain 29.6 mg of a black solid.

The subsequent process was carried out in accordance with the procedure of Step 1 of Example 1 to obtain 12 mg (yield 29.6%) of the title compound.

Step 2: Preparation of $C_{60}O_{40}Mn_{12}$

The procedure of Step 2 of Example 1 was repeated except that the liquid phase and wash solutions generated during the process of Step 1 of Example 2 were used, to obtain 10.5 mg (yield 31.2%) of the title compound.

Step 3: Preparation of $C_{60}O_{15}Mn_8$

The procedure of Step 3 of Example 1 was repeated except that the liquid phase and the wash solutions generated during the process of Step 2 of Example 2 were used, to obtain 8.5 mg (yield 36.4%) of the title compound.

Total yield was 29.6+31.2+36.4=97.2%.

Characteristics of the Compounds of Formula (I)

Analyses of the products of Example 1 were performed by a scanning electron microscopy (SEM), X-ray photoelectron spectroscopes (XPS), transmission electron microscopy (TEM), $H^1$ NMR, Solid-state $^{13}C$ NMR, mass spectrometer (MS), infrared (IR) spectra, $N_2$ adsorption/desorption, and differential thermal analysis and thermogravimetric analysis (DTA-TGA) to determine the structure, chemical functional groups, the composition and the physical properties of the $oxyC_{60}$ nanospheres prepared by the process of the present invention.

(1) SEM and HR-TEM Analysis

Figure 2A:
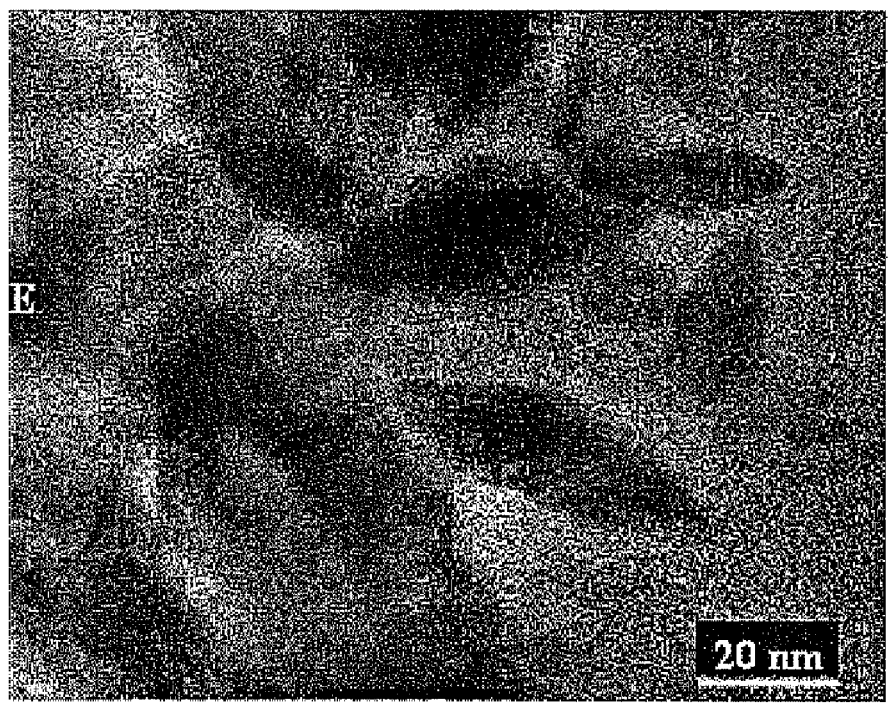
FIGS. 2A to 2B: High-resolution transmission electron microscopy (HR-TEM) images of $oxyC_{60}$ prepared in Step 1 of Example 1.
Figure 2B:
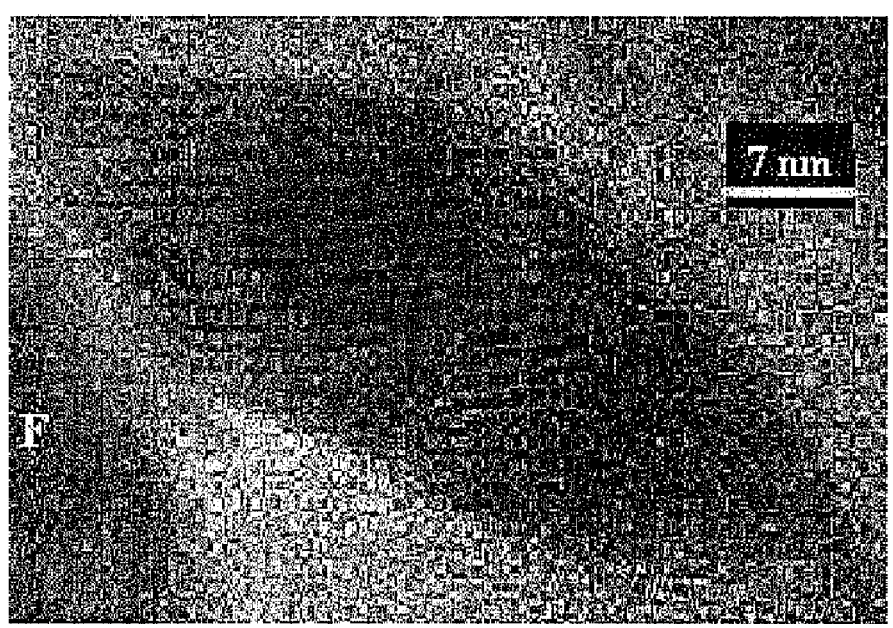

The results of SEM and HR-TEM analyses of the $OxyC_{60}$ nanosphere obtained in Step 1 of Example 1 are shown in FIGS. 1 (A-D) and FIGS. 2 (A, B), respectively. FIG. 1 and FIG. 2 clearly show that the geometrical structure of the complexes is olivary (2A, 2B), and those long-olivary complexes are assembled to form $oxyC_{60}$ nanospheres (1A, 1B). Also, some of the nanospheres are perfectly spherical and others have the shape of a soccer ball (1C), and such nanospheres also are connected with each other to constitute coralloid-like aggregates (1D).

Figure 3:
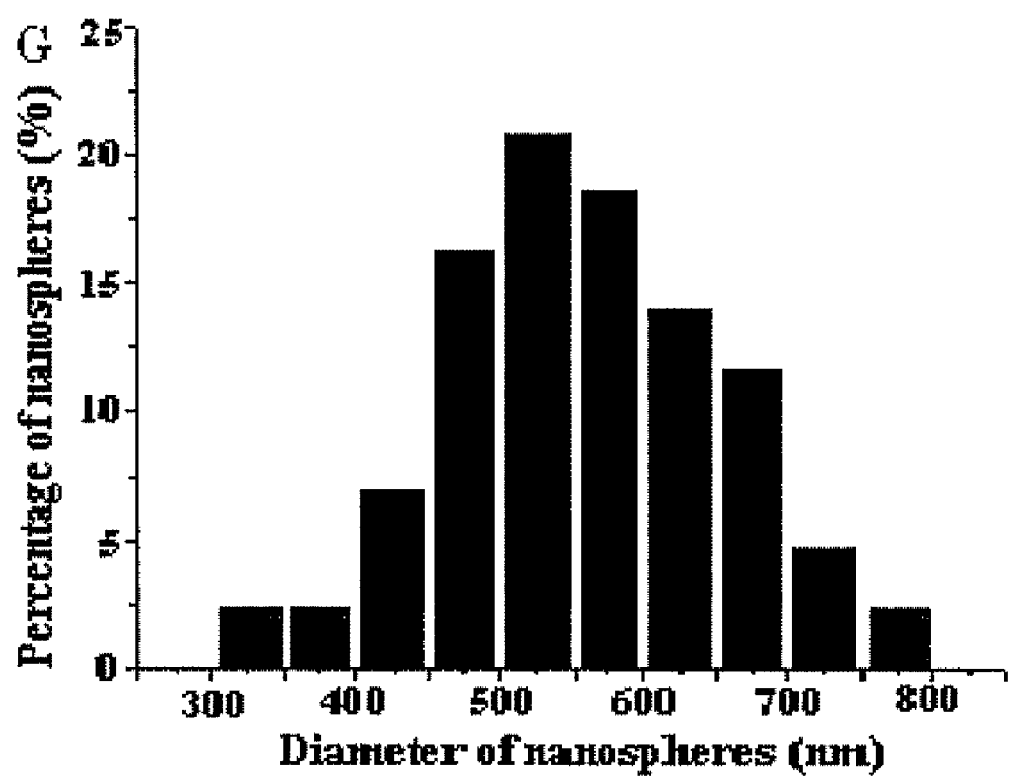
FIG. 3: Particle size distribution of $oxyC_{60}$ prepared in Step 1 of Example 1.
Figure 4:
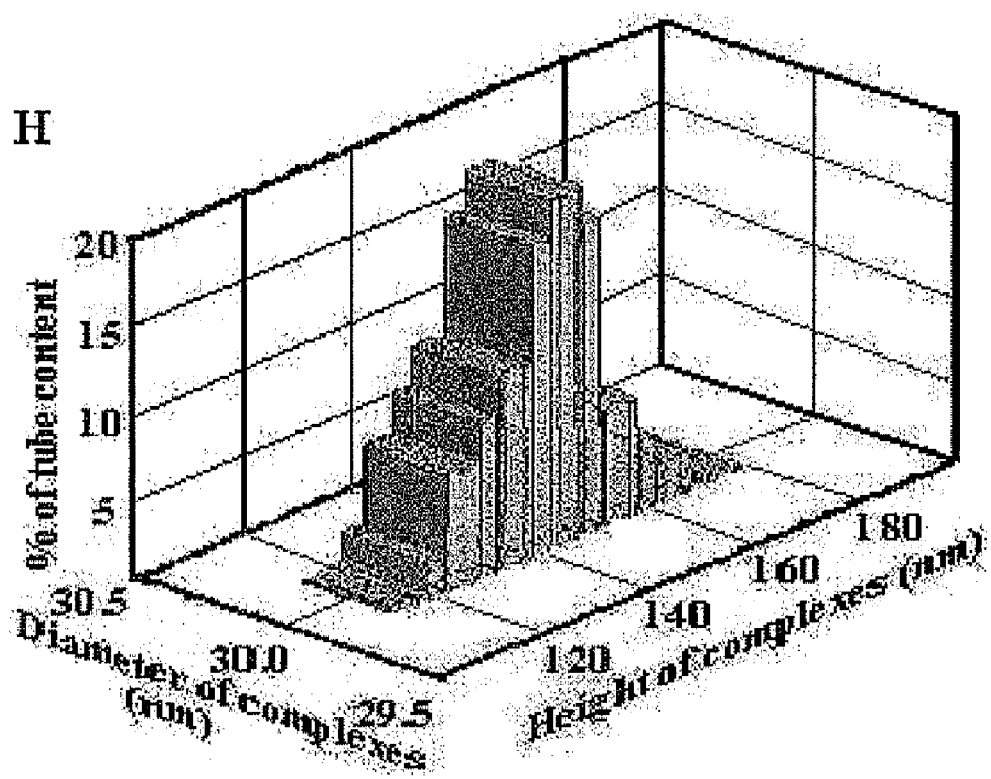
FIG. 4: Size distribution of olivary complexes in $oxyC_{60}$.

FIG. 3 and FIG. 4 show the particle size distribution of $oxyC_{60}$ prepared in Step 1 of Example 1 and the size distribution of the olivary complexes of the $oxyC_{60}$, respectively.

(2) IR Spectra

Figure 5:
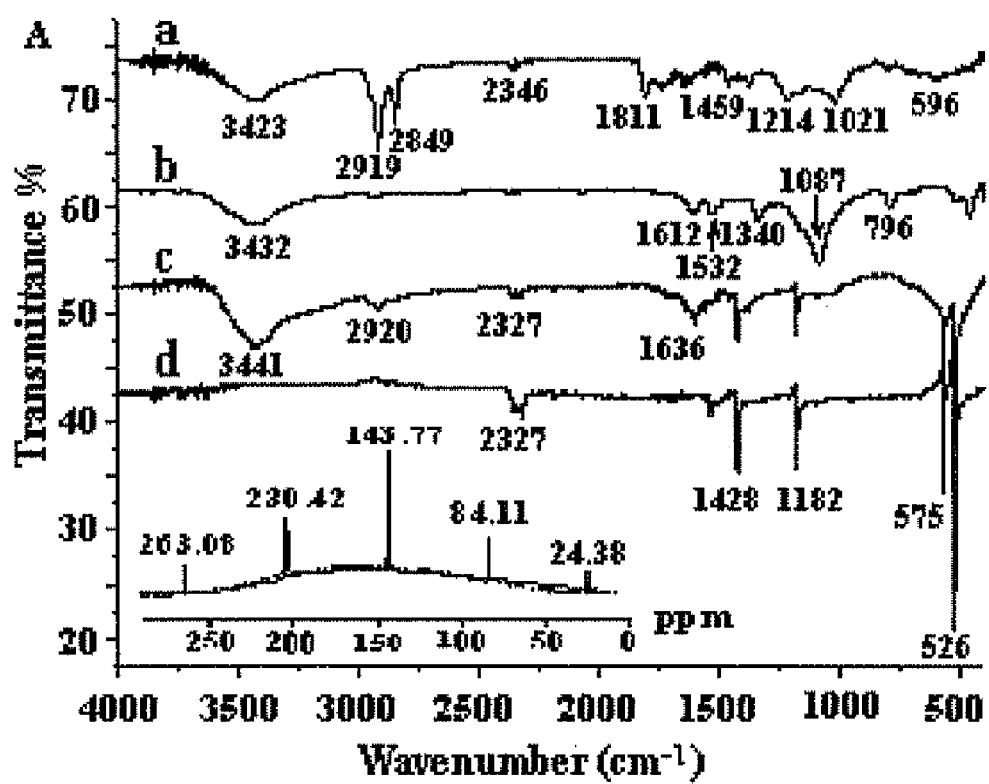
FIG. 5: Infrared (IR) spectra of acetyl $oxyC_{60}$ nanosphere (a), nanosphere-2,4-dinitrophenylhydrazone (b), $oxyC_{60}$ prepared in Step 1 of Example 1 (c), and fullerene ($C_{60}$) (d); and Solid-state $^{13}$C-nuclear magnetic resonance (NMR) spectrum of $oxyC_{60}$ prepared in Step 1 of Example 1 (insert)

IR spectra of acetyl $oxyC_{60}$ nanospheres (5a), nanospheres-2,4-dinitro-phenylhydrazone (5b), $oxyC_{60}$ nanospheres obtained in Step 1 of Example 1 (5c) and $C_{60}$ (5d) are shown in FIG. 5, respectively.

As compared with the peaks for the $oxyC_{60}$ nanospheres of Example 1 (5c), new peaks representing —$COCH_3$ groups appear in the spectrum of acetyl $oxyC_{60}$ (5a) at 2914 $cm^{-1}$ (C—H stretching), 2849 $cm^{-1}$ (C—H stretching), 1803 $cm^{-1}$ (carbonyl in esters), 1241 $cm^{-1}$ (C=O stretching) and 1017 $cm^{-1}$ (C=O stretching). The broad peak of acetyl $oxyC_{60}$ (5a) at ~3420 $cm^{-1}$ is weaker than that of $oxyC_{60}$ (5c) but clearly present, which suggests that other inorganic elements may also exist in the $oxyC_{60}$ nanospheres. In particular, no hydrogen atoms attached to the framework of the $oxyC_{60}$ nanospheres obtained in Step 1 of Example 1 were detected, which was also confirmed by solid-state $H^1$ NMR or liquid (DCl) $H^1$ NMR spectroscopies.

The $oxyC_{60}$ nanospheres obtained in Step 1 of Example 1 were also analyzed by solid-state 6 kHz $^{13}C$ NMR. The result exhibits four distinct carbon peaks, as shown in the insert of FIG. 5, two of them having chemical shift centers at δ203.42 ppm and δ84.11 ppm which correspond to α, β-unsaturated ketone carbons and ether (R—O—R) or hydroxyl carbons, respectively. The third downfield peak at δ264.08 ppm is assigned to the carbons directly coordinated with manganese dioxides, and the prominent peak at δ143.78 ppm, to the basic framework of $C_{60}$ retained in the $oxyC_{60}$ nanospheres. The retained $C_{60}$ from framework was also supported by the observed base peak at 766 in a solution mass spectrum (MS) scan.

(3) X-Ray Photoelectron Spectra (XPS)

Figure 6:
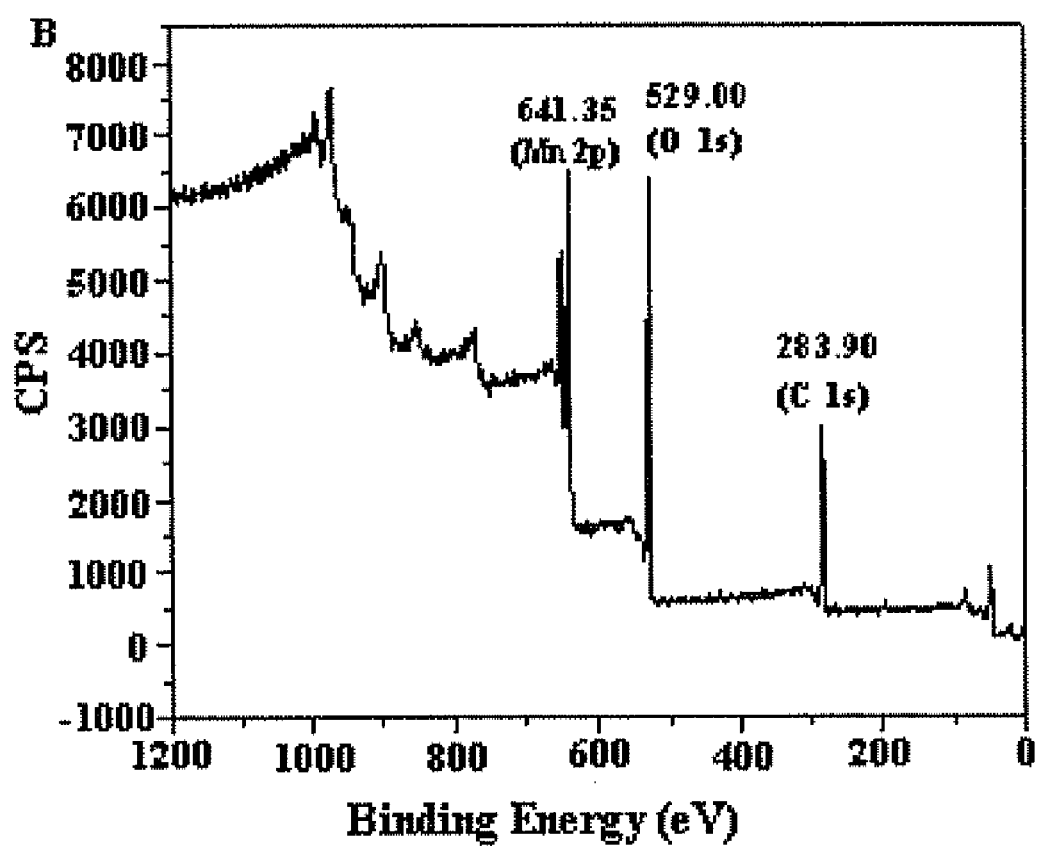
FIG. 6: An X-ray photoelectron spectrum (XPS) of $oxyC_{60}$ prepared in Step 1 of Example 1.

The chemical composition in the oxyC$_{60}$ nanosphere obtained in Step 1 of Example 1 was evaluated by X-ray photoelectron spectroscopes (XPS), and the results are shown in FIG. 6 and Table I.

TABLE I

| Peak | Central peak BE (eV) | FWHM (eV) | Percentage % | Elem. No. in monomer |
|---|---|---|---|---|
| Mn 2p$_{3/2}$ | 641.35 | 2.683 | 12.66 | ~16 |
| O 1s | 529.00 | 1.263 | 40.82 | ~53 |
| C 1s | 283.90 | 1.725 | 46.53 | 60 |

Along with the results in FIG. 6 and Table 1, the overall XPS, MS, solid-state H$^1$ NMR and liquid (DCl) H$^1$ NMR data suggest that the molecular formula of the oxyC$_{60}$ nanosphere is C$_{60}$O$_{53}$Mn$_{16}$, which was also verified by TGA analysis.

Figure 7A:
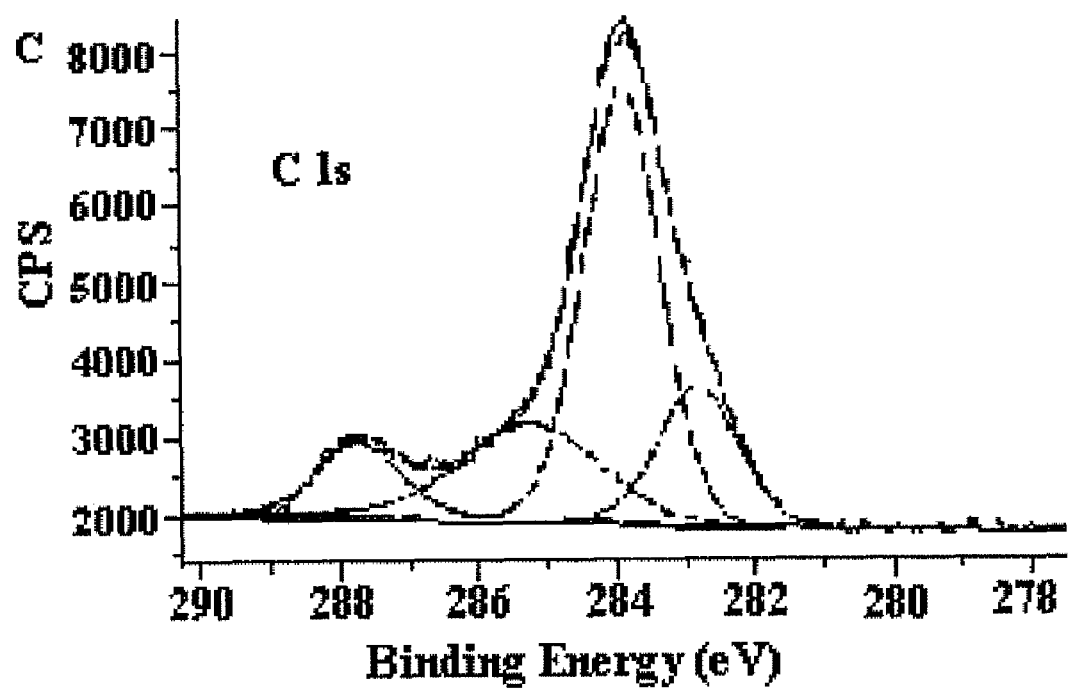
FIGS. 7A to 7C: C 1s region, O 1s region and Mn 2p region curve fittings, repectively, of $oxyC_{60}$ prepared in Step 1 of Example 1.
Figure 7B:
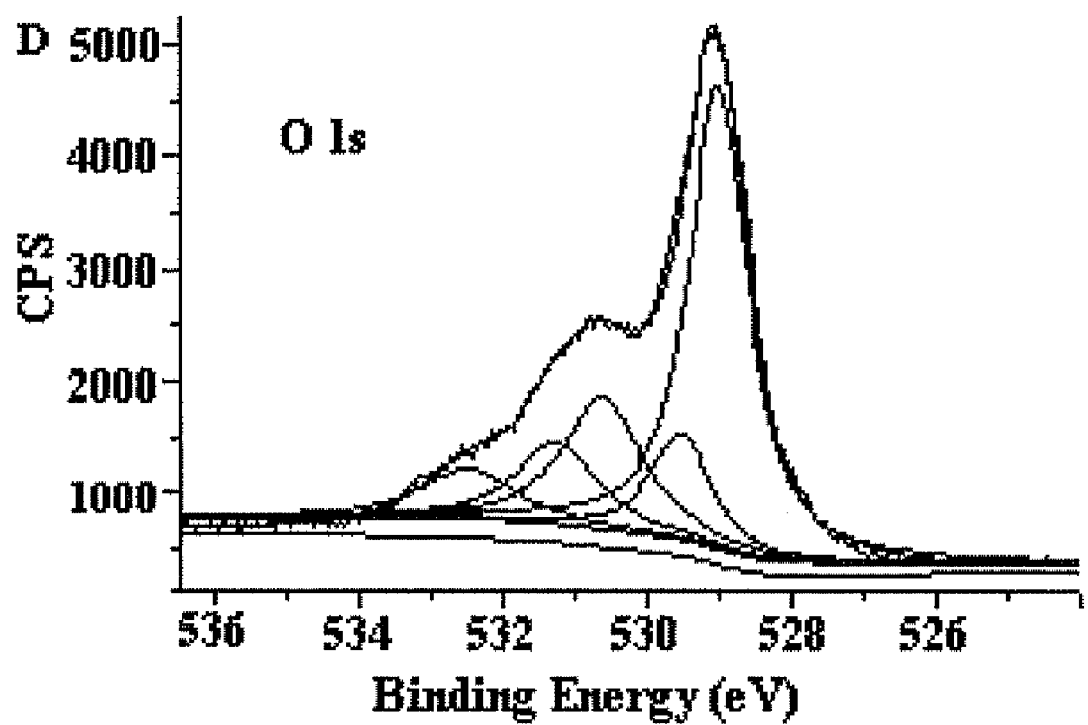
Figure 7C:
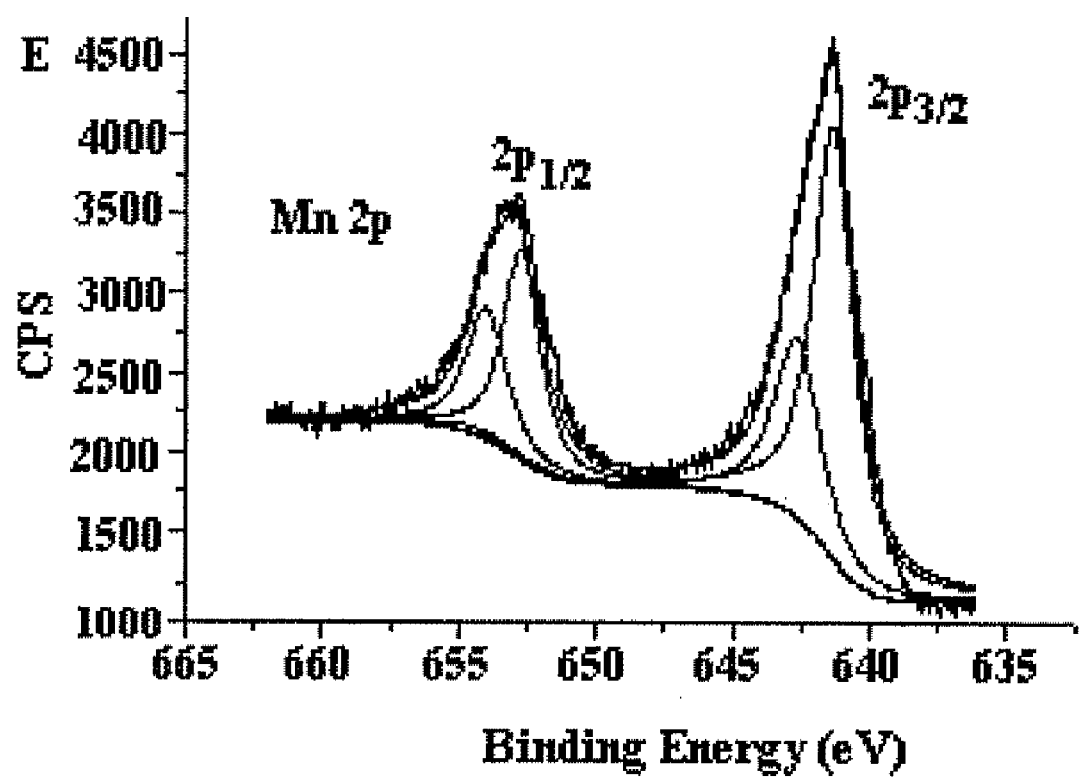

The local electronic environments of C, O and Mn atoms of the oxyC$_{60}$ nanosphere obtained in Step 1 of Example 1 were evaluated by curve fitting the XPS core chemical shifts, so as to identify their binding states in the oxyC$_{60}$ nanosphere. The curve fitting results of C 1s, O 1s and Mn 2p are shown in FIGS. 7A, 7B and 7C, respectively.

In evaluating the chemical shifts of the oxyC$_{60}$ nanosphere, reference materials (a~g) listed in Table II were selected as standard references: C$_{60}$ (d) and p-benzoquinone (a) were chosen as standards for the framework of oxidized C$_{60}$ and ketone moieties, respectively; inositol (c) and hydroquinone (f), for Z-1,2-dioxylcyclo hexadiene-3,5 moiety; Mn(C$_5$H$_5$)$_2$ (e), for Mn coordinated to double bonds; MnO$_2$ (g), for Mn; and Fullerols (b), for hemiketal.

The results by curve fitting of C 1s, O 1s and Mn 2p$_{3/2}$ peaks of the in oxyC$_{60}$ nanosphere obtained in Step 1 of Example 1 and standard data of reference materials are shown in Table II.

TABLE II

| | Curve fitting | | Standards | Monomer (oxyC$_{60}$) | |
|---|---|---|---|---|---|
| Elem. | BE (eV) | % | BE (eV) | Groups | Number |
| C 1s | 287.7 | 9.2 | 287.4$^a$ 289.7$^b$ | O—C—O | 5.5 |
| | 285.3 | 20.4 | 286.4$^c$ 287.9$^b$ | C—O | 12.2 |
| | 283.9 | 52.5 | 284.5$^d$ 286.1$^b$ | ⅓C═C—C | 31.5 |
| | 282.8 | 17.8 | 284.6$^e$ | ½(C═C)Mn | 10.7 |
| O 1s | 532.5 | 7.8 | 533.5$^f$ | (C—O)Mn | 4.1 |
| | 531.2 | 11.5 | | (C—O*)C═O | 6.1 |
| | 530.4 | 20.7 | 532.2$^a$ | ½(O—C—O) | 10.8 |
| | 529.0 | 60.0 | 530.0$^g$ | ½MnO$_2$ | 31.8 |
| Mn | 642.7 | 36.4 | 642.2$^g$ | (C—O)MnO$_2$ | 5.9 |
| 2p$_{3/2}$ | 641.3 | 63.5 | 638.5$^e$ | (C═C)MnO$_2$ | 10.4 |

$^a$p-benzoquinone;
$^b$fullerols;
$^c$inositol;
$^d$C60;
$^e$Mn(C$_5$H$_5$)$_2$;
$^f$hydroquinone;
$^g$MnO$_2$ As shown in Table II and FIG. 7A, the C 1s region curve fitting exhibits four component peaks. The peak with the highest binding energy (BE) at 287.72 eV (9.24%) is assigned to di-oxygenated carbons having the lowest electron density around them because this BE value is similar to that of p-benzoquinone (297.4 eV). The peak at 285.25 eV (21.41%) corresponds to mono-oxygenated carbons, and the peak at 283.92 eV (52.51%), to framework carbons. The smallest BE peak at 282.8 eV (17.8%) is assigned to carbon double bond coordinated to Mn, because such double bond would have higher electron density than other carbons of the framework.

As shown in FIG. 7B and Table II, the O 1s region curve fitting also reveals four component peaks. As the electronegativity (1.60) of Mn is much less than that (2.50) of carbon, the peak of the highest BE (532.5 eV, 7.8%) is assigned to the oxygen of (C—O) bound to Mn; and the peak at 531.2 eV (11.5%), to the oxygen of carbonyl carbons of hemiketal or ketal groups formed by inter- or intra-condensation of hydroxyl in Z-1,2-dioxylcyclohexadiene-3,5 moieties having ketone groups. In addition, the peak at 530.4 eV (20.7%) corresponds to the oxygen of O—C—O group; and the smallest BE peak at 529.7 eV (60.0%), to the oxygen of MnO$_2$.

Further, the Mn 2p curve fitting showed 2 component peaks as shown in FIG. 7C and Table II. The peak at 642.7 eV (36.4%) corresponds to the MnO$_2$ manganese bound to the oxygen atom of C—O or O—C—O; and the other peak at 641.3 eV (63.5%), to the MnO$_2$ manganese bound to carbon double bonds. This result was deduced considering that the Mn bound to O should have lower electron density than the Mn bound to C because the electronegativity of O (3.50) is larger than that of C (2.50).

(4) SEM Analysis

Figure 8A:
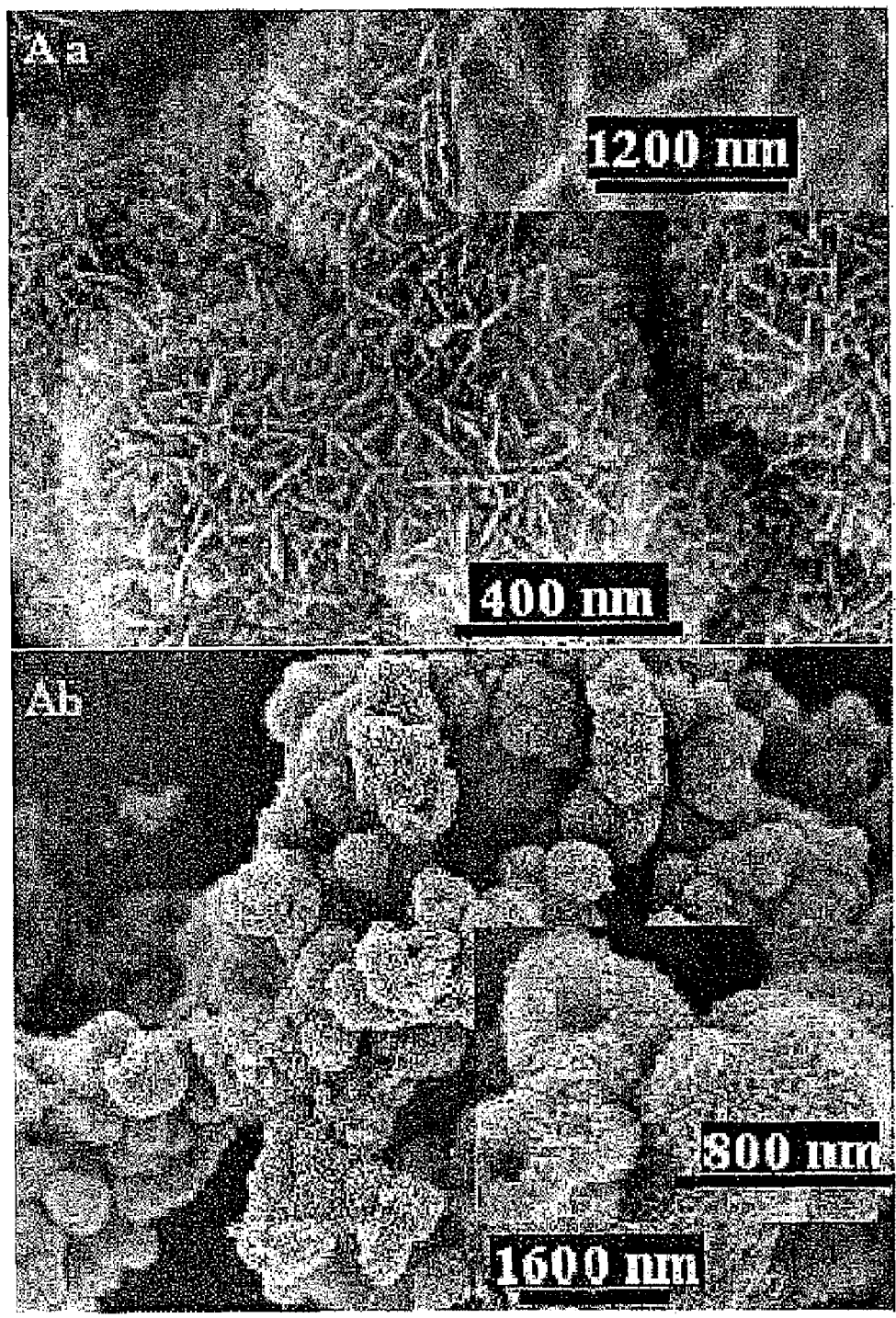
FIGS. 8A to 8C: SEM images of $oxyC_{60}$ prepared in Step 1, Step 2 and Step 3 of Example 1, respectively.
Figure 8B:
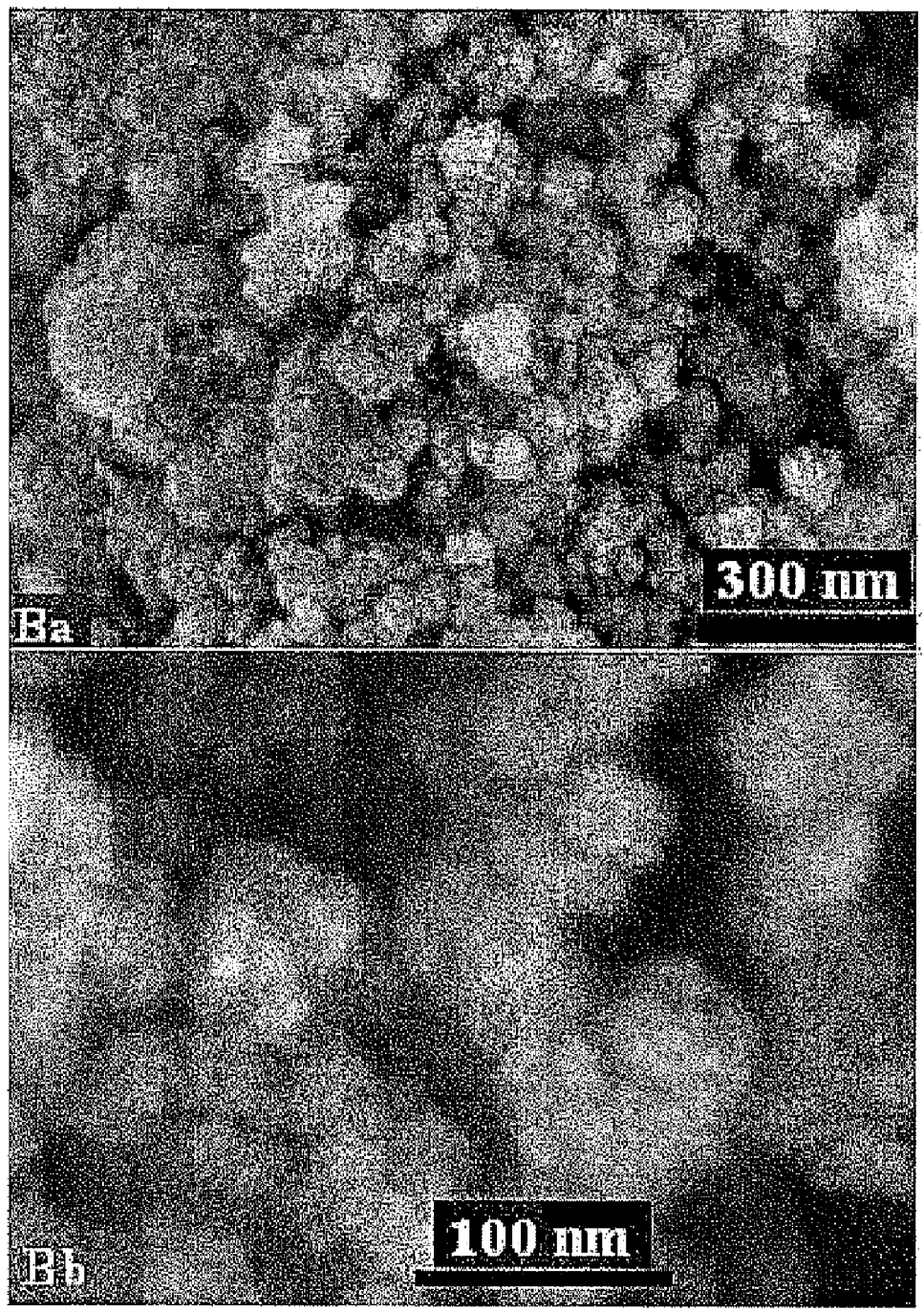
Figure 8C:
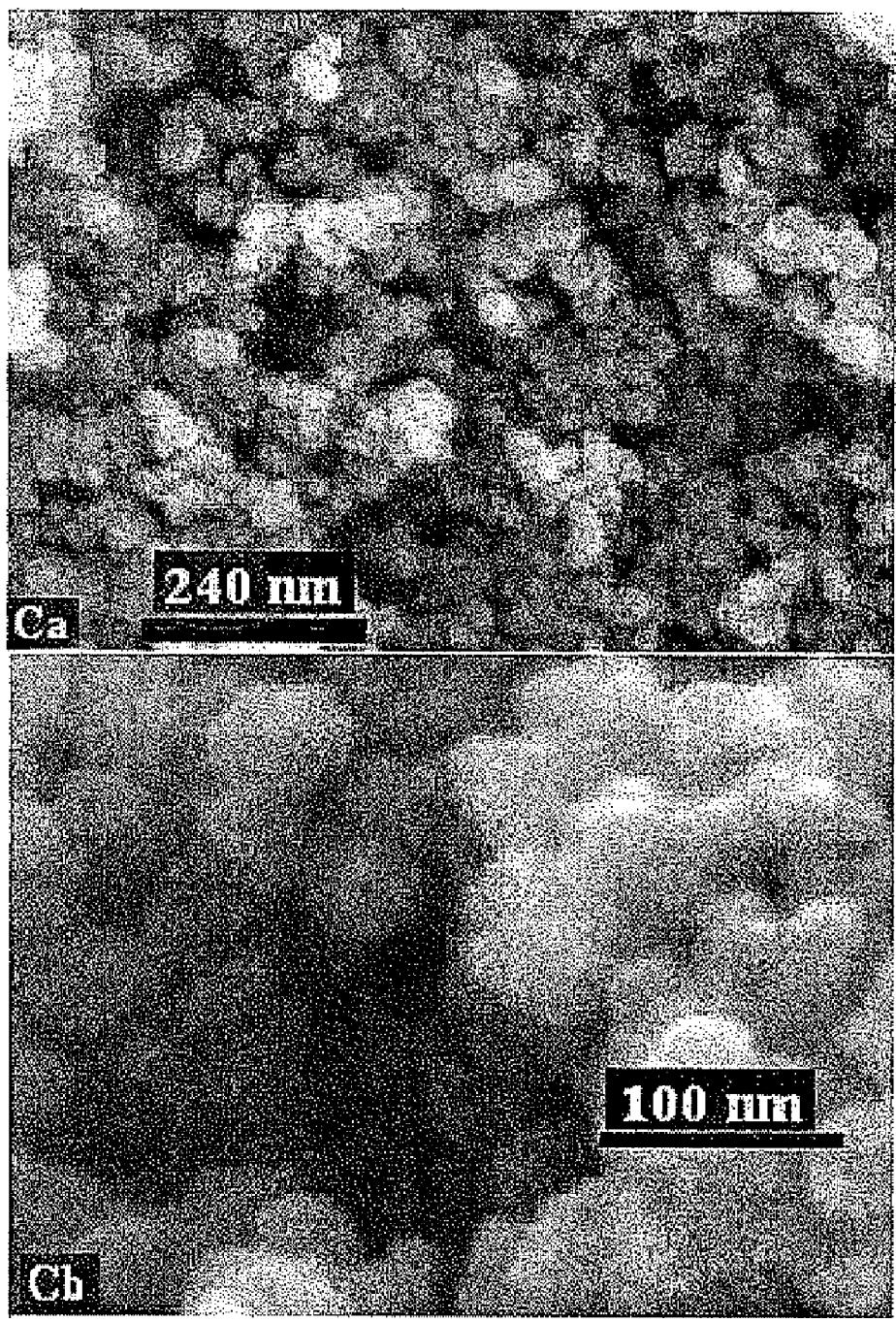

The SEM images of the oxyC$_{60}$ nanospheres prepared in Step 1, Step 2 and Step 3 of Example 1 are shown in FIG. 8 (A-C). The results show that C/O/Mn compositions of the oxyC$_{60}$s of Step 1 (8A), 2 (8B) and 3 (8C) are 45.1/39.7/15.2, 53.9/35.7/10.4 and 60.1/32.1/7.67, respectively.

(5) Analysis of N$_2$ Adsorption/Desorption Isotherm and DTA-TGA

Figure 9:
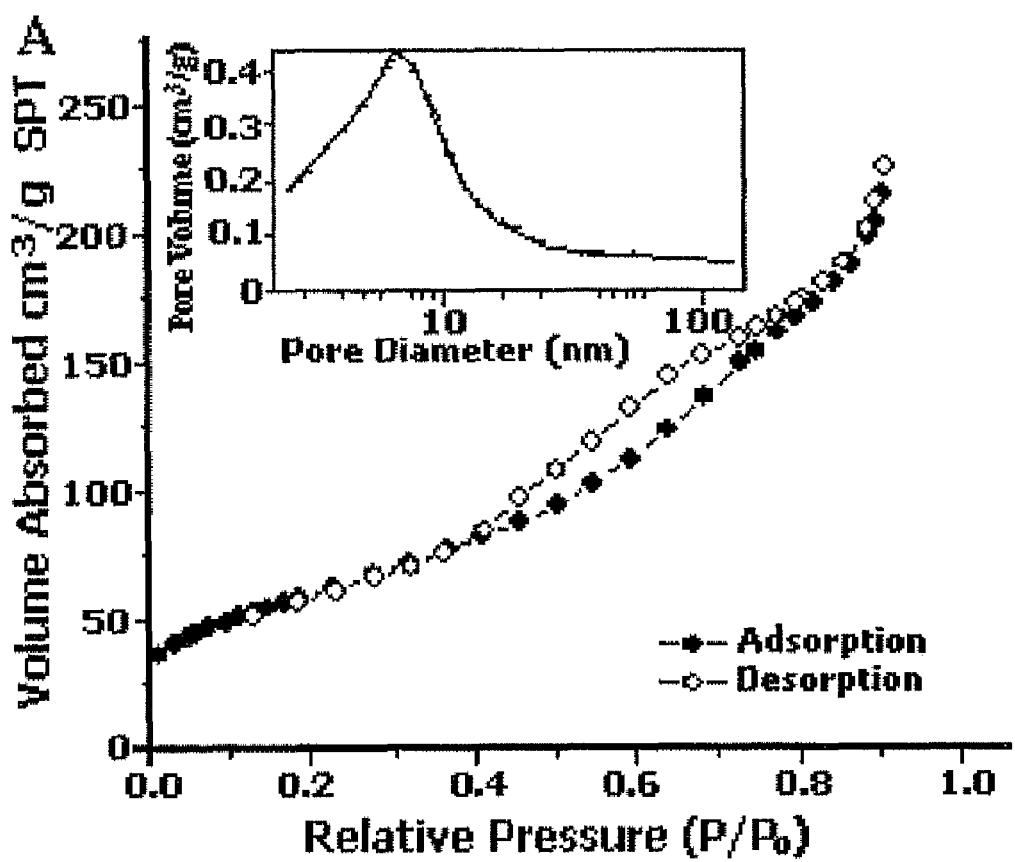
FIG. 9: $N_2$ adsorption/desorption isotherms and pore size distribution of $oxyC_{60}$ prepared in Step 1 of Example 1.

The N$_2$ adsorption/desorption isotherm and pore size distribution of the oxyC$_{60}$ obtained in Step 1 of Example 1 illustrated in FIG. 9, demonstrates that oxyC$_{60}$ nanospheres prepared in the present invention have a large surface area.

Figure 10:
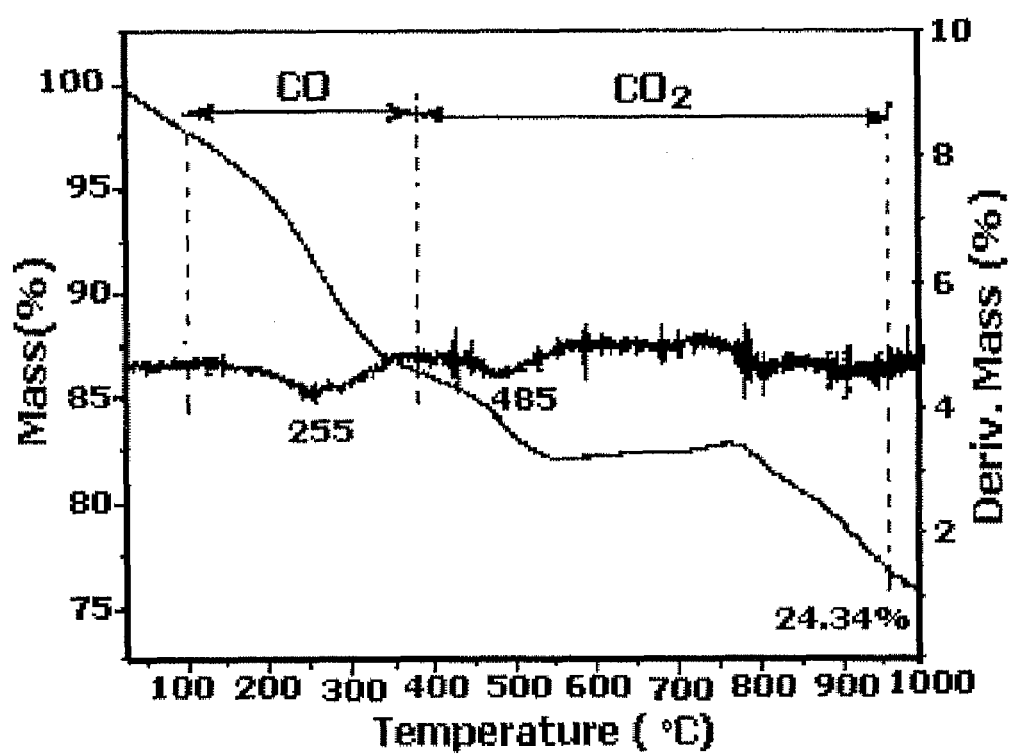
FIG. 10: Differential thermal analysis and thermogravimetric analysis (DTA-TGA) curve of $oxyC_{60}$ prepared in Step 1 of Example 1.

Further, DTA-TGA results in FIG. 10 show that more than 80% of the mass of oxy C$_{60}$ prepared in Step 1 of Example 1 is retained until the temperature reaches 800° C., while the release of CO and CO$_2$ during the thermal treatment suggests that oxyC$_{60}$ prepared in the present invention consists mainly of mono-oxygenated and di-oxygenated carbons.

As can be seen from the above, the novel oxyC$_{60}$ nanosphere of the present invention having a large surface area and high thermal stabiliy can be advantageously used in various fields including medical science and pharmaceutical chemistry.

While the invention has been described with respect to the specific embodiments, it should be recognized that various modifications and changes may be made by those skilled in the art to the invention which also fall within the scope of the invention as defined by the appended claims.

What is claimed is:

1. An oxyfullerene hollow nanosphere defined in accordance with the following formula (I):

$$C_xO_yMn_z \qquad (I)$$

wherein x, y, and z are atomic percentages in the ranges of 45 to 72, 18 to 42 and 7 to 16, respectively, based on x+y+z=100.

2. A method for preparing the oxyfullerene hollow nanosphere of formula (I) recited in claim 1 comprising (i) reacting a fullerene with an alkali metal hydroxide, and potassium permanganate (KMnO$_4$) or manganese dioxide (MnO$_2$); (ii) treating the solid obtained in step (i) with an acidic solution;

and (iii) removing the liquid phase to collect the solid obtained in step (ii), followed by washing the solid.

3. The method of the claim 2, further comprising the steps of (iv) combining the liquid phase and the wash solution separated in step (iii); (v) treating the resulting mixture with an alkaline aqueous solution to induce precipitation; and (vi) collecting and washing the solid obtained in step (v), and optionally (vii) repeating the procedures of steps (iv) to (vi).

4. The method of the claim 2, wherein the fullerene is reacted simultaneously or successively with the alkali metal hydroxide and $KMnO_4$ or $MnO_2$ in step (i).

5. The method of the claim 2, wherein the alkali metal hydroxide used in step (i) is potassium hydroxide (KOH) or sodium hydroxide (NaOH).

6. The method of the claim 2, wherein the alkali metal hydroxide used in step (i) is employed in amounts of 12 to 20 folds by weight based on the weight of the fullerene.

7. The method of the claim 2, wherein $KMnO_4$ or $MnO_2$ used in step (i) is employed 3 to 6 folds by weight based on the weight of the fullerene.

8. The method of the claim 2, wherein the acidic solution used in step (ii) is concentrated HCl.

9. The method of the claim 3, wherein the alkaline aqueous solution used in step (v) is aqueous NaOH.

* * * * *